(12) United States Patent
Mukherjee et al.

(10) Patent No.: US 10,233,200 B2
(45) Date of Patent: Mar. 19, 2019

(54) ORGANOMODIFIED MONOSILYL COMPOUND, ITS PREPARATION AND APPLICATIONS THEREOF

(71) Applicant: Momentive Performance Materials Inc., Waterford, NY (US)

(72) Inventors: Narayan Mukherjee, Croton-on-Hudson, NY (US); George A Policello, Ossining, NY (US)

(73) Assignee: Momentive Performance Matericals Inc., Waterford, NY (US)

( * ) Notice: Subject to any disclaimer, the term of this patent is extended or adjusted under 35 U.S.C. 154(b) by 0 days.

(21) Appl. No.: 15/681,750

(22) Filed: Aug. 21, 2017

(65) Prior Publication Data

US 2019/0055271 A1    Feb. 21, 2019

(51) Int. Cl.
| | | |
|---|---|---|
| *C07F 7/08* | (2006.01) | |
| *A01N 25/24* | (2006.01) | |
| *A01N 37/10* | (2006.01) | |
| *A01N 25/02* | (2006.01) | |

(52) U.S. Cl.
CPC .............. *C07F 7/081* (2013.01); *A01N 25/02* (2013.01); *A01N 25/24* (2013.01); *A01N 37/10* (2013.01)

(58) Field of Classification Search
None
See application file for complete search history.

(56) References Cited

U.S. PATENT DOCUMENTS

| | | | |
|---|---|---|---|
| 3,159,604 A | 12/1964 | Ashby | |
| 3,220,972 A | 11/1965 | Lamoreaux | |
| 3,299,112 A | 1/1967 | Bailey | |
| 3,715,334 A | 2/1973 | Karstedt | |
| 3,775,452 A | 11/1973 | Karstedt | |
| 3,814,730 A | 6/1974 | Karstedt | |
| 5,430,166 A | 7/1995 | Klein et al. | |
| 5,430,167 A | 7/1995 | Klein et al. | |
| 5,558,806 A | 9/1996 | Policello et al. | |
| 5,674,832 A | 10/1997 | Keys | |
| 6,255,511 B1 | 7/2001 | Klein et al. | |
| 6,706,840 B1 | 3/2004 | Williams | |
| 7,700,797 B2 | 4/2010 | Leatherman et al. | |
| 7,872,053 B2 | 1/2011 | Wagner et al. | |
| 2007/0249560 A1 | 10/2007 | Leatherman et al. | |
| 2007/0269467 A1 | 11/2007 | Leatherman et al. | |
| 2010/0215922 A1 | 8/2010 | Rajaraman et al. | |
| 2012/0251832 A1* | 10/2012 | Huang ................ C08G 65/336 428/447 |
| 2017/0280713 A1 | 10/2017 | Policello et al. | |

FOREIGN PATENT DOCUMENTS

| | | |
|---|---|---|
| EP | 0710500 B1 | 10/1995 |
| WO | 2014186658 A1 | 11/2014 |

OTHER PUBLICATIONS

International Search Report and Written Opinion dated Dec. 20, 2018.

* cited by examiner

*Primary Examiner* — Clinton A Brooks
*Assistant Examiner* — Kofi Adzamli
(74) *Attorney, Agent, or Firm* — Joseph S. Ostroff

(57) ABSTRACT

Organomodified monosilyl compounds as defined herein exhibit excellent resistance to hydrolysis over a wide range of pH and excellent wetting properties. The organomodified monosilyl compounds are advantageously employed as wetting agents in any of a wide variety of products such as agrochemical compositions, cosurfactants, coatings, personal care products and home care products.

21 Claims, No Drawings

US 10,233,200 B2

ORGANOMODIFIED MONOSILYL COMPOUND, ITS PREPARATION AND APPLICATIONS THEREOF

FIELD OF THE INVENTION

The present invention relates to organomodified monosilyl compounds exhibiting resistance to hydrolysis over a wide pH range. More particularly, the present invention relates to hydrolysis-resistant organomodified monosilyl compounds having resistance to hydrolysis over a pH ranging from about 2 to about 12. The present invention also relates to such hydrolysis-resistant organomodified monosilyl compounds as components of agricultural, cosmetic, home care and coating compositions.

BACKGROUND OF THE INVENTION

The topical application of liquid compositions to the surfaces of both animate and inanimate objects to effect a desired change involve processes of controlling wetting, spreading, foaming, detergency, and the like. When used in aqueous solutions to improve the delivery of active ingredients to the surface being treated, trisiloxane-type compounds have been found to be useful in enabling the control of these processes to achieve the desired effect. However, trisiloxane compounds can only be used within a narrow pH range, one ranging from a slightly acidic pH of 6 to a very mildly basic pH of 7.5. Outside this narrow pH range, trisiloxanes are not stable to hydrolysis, undergoing rapid decomposition.

Silicon based surfactants that are stable to hydrolysis over a wide pH range are very desirable as such compounds would allow for compositions providing more effective topical application to the surfaces of both animate and inanimate objects, the use of smaller quantities of water and/or an increase in the effectiveness of agricultural sprays.

SUMMARY OF THE INVENTION

In accordance with the present invention, there is provided an organomodified monosilyl compound of the general formula:

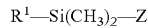

$$R^1 - Si(CH_3)_2 - Z$$

wherein:

$R^1$ is branched monovalent hydrocarbon group of from 5 to 8 carbon atoms containing at least two methyl groups;

Z is $R^2$ or $R^3$;

$R^2$ is $CH_2CH_2CH_2 - O - (C_2H_4 - O)_a(C_3H_6O)_b(C_4H_8O)_c - R^4$ in which $R^4$ is hydrogen, a linear or branched monovalent hydrocarbon group of from 1 to about 4 carbon atoms or an acyl group, subscript a is from 1 to about 20, subscript b is from 0 to about 19, subscript c is from 0 to about 19 and the sum of subscripts a, b and c is from 1 to about 20; and, $R^3$ is $-CH_2CH_2CH_2 - O - CH(OH)CH_2 - N^+(CH_3)_2 - R^5$ [$X^-$] in which $R^5$ is a linear or branched hydrocarbon group of from 1 to about 4 carbon atoms or an acetyl group and $X^-$ is a saturated or unsaturated carboxylate anion of from 2 to about 22 carbon atoms optionally containing 1 or 2 hydroxyl groups.

The organomodified monosilyl compound of the invention may be incorporated in numerous types of compositions, e.g., agricultural compositions, cosmetic compositions, home care compositions and coating compositions, to which its excellent stability over a wide range of pH and outstanding wetting properties impart considerable functional advantages.

DETAILED DESCRIPTION OF THE INVENTION

In the specification and claims herein, the following terms and expressions are to be understood as indicated.

The singular forms "a," "an," and "the" include the plural, and reference to a particular numerical value includes at least that particular value, unless the context clearly dictates otherwise.

Other than in the working examples or where otherwise indicated, all numbers expressing amounts of materials, reaction conditions, time durations, quantified properties of materials, and so forth, stated in the specification and claims are to be understood as being modified in all instances by the term "about".

All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

The terms, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

It will be understood that any numerical range recited herein includes all sub-ranges within that range and any combination of the various endpoints of such ranges or sub-ranges.

As used herein, integer values of stoichiometric subscripts refer to molecular species and non-integer values of stoichiometric subscripts refer to a mixture of molecular species on a molecular weight average basis, a number average basis or a mole fraction basis.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

The term "adjuvant" means any composition, material or substance which increases the efficacy of a bioactive material.

The term "bioactive" refers to an agricultural chemical or material, including but not limited to pesticides, e.g., herbicides, fungicides, insecticides, acaricides and molluscides; plant nutrients; defoliants; and, plant growth regulators.

The expression "hydrocarbon group" means any hydrocarbon from which one or more hydrogen atoms has been removed and is inclusive of alkyl, alkenyl, alkynyl, cyclic alkyl, cyclic alkenyl, cyclic alkynyl, aryl, aralkyl and arenyl groups and is inclusive of hydrocarbon groups containing at least one heteroatom.

The term "alkyl" means any monovalent, saturated straight, branched or cyclic hydrocarbon group; the term "alkenyl" means any monovalent straight, branched, or cyclic hydrocarbon group containing one or more carbon-carbon double bonds where the site of attachment of the group can be either at a carbon-carbon double bond or elsewhere therein; and, the term "alkynyl" means any monovalent straight, branched, or cyclic hydrocarbon group containing one or more carbon-carbon triple bonds and, optionally, one or more carbon-carbon double bonds, where the site of attachment of the group can be either at a carbon-carbon triple bond, a carbon-carbon double bond or elsewhere therein. Examples of alkyls include methyl, ethyl, propyl and isobutyl. Examples of alkenyls include vinyl, propenyl, allyl, methallyl, ethylidenyl norbornane, ethylidene norbornyl, ethylidenyl norbornene and ethylidene norbornenyl. Examples of alkynyls include acetylenyl, propargyl and methylacetylenyl.

In some embodiments of organomodified monosilyl compound $R^1$—Si(CH$_3$)$_2$—Z, $R^1$ is a branched alkyl group $CR^6R^7R^8(CR^9R^{10})_m(CR^{11}R^{12})_n CHR^{13}CH_2$— in which $R^6$, $R^7$, $R^8$, $R^9$, $R^{10}$, $R^{11}$, $R^{12}$ and $R^{13}$ each independently is hydrogen or methyl, from 2 to 4 of $R^6$, $R^7$, $R^8$, $R^9$, $R^{10}$, $R^{11}$, $R^{12}$ and $R^{13}$ are methyl and subscripts m and n each independently is 0 or 1.

In other embodiments of organomodified monosilyl compound $R^1$—Si(CH$_3$)$_2$—Z, $R^1$ contains from 2 to 4 methyl groups, $CR^6R^7R^8$ is H$_3$C—, (H$_3$C)$_2$CH— or (H$_3$C)$_3$C—, subscripts m and/or n are 0, Z is $R^2$ and $R^2$ is —CH$_2$CH$_2$CH$_2$—O—(C$_2$H$_4$O)$_a$(C$_3$HO)$_b$—$R^4$ in which $R^4$ is hydrogen, linear or branched alkyl of from 1 to 4 carbon atoms or an acyl group, subscript a is from 1 to about 20, preferably from 2 to about 15 and more preferably from 4 to about 10, subscript b is 0 or from 1 to about 10, preferably 0 or from 1 to about 6 and more preferably 0 or from 1 to about 4, and the sum of subscripts a and b is from 1 to about 20, preferably from 2 to about 15 and more preferably from 4 to about 10.

In still other embodiments of organomodified monosilyl compound $R^1$—Si(CH$_3$)$_2$—Z, $R^1$ contains from 2 to 4 methyl groups, $CR^6R^7R^8$ is H$_3$C—, (H$_3$C)$_2$CH— or (CH$_3$)$_3$C—, m is 0 or 1, n is 0, Z is $R^2$ and $R^2$ is —CH$_2$CH$_2$CH$_2$—O—(C$_2$H$_4$O)$_a$—$R^4$ in which $R^4$ is hydrogen, linear or branched alkyl of from 1 to 4 carbon atoms or an acyl group, and subscript a is from 1 to about 20, preferably from 2 to about 15 and more preferably from 4 to about 10.

In further embodiments of organomodified monosilyl compound $R^1$—Si(CH$_3$)$_2$—Z, $CR^6R^7R^8$ is H$_3$C—, (H$_3$C)$_2$CH— or (H$_3$C)$_3$C—, m and/or n are 0 or 1, Z is $R^3$ and $R^3$ is —CH$_2$CH$_2$CH$_2$—O—CH$_2$(OH)—CH$_2$—N$^+$(CH$_3$)$_2$—$R^5$ [X$^-$] in which $R^5$ is a linear or branched alkyl of from 1 to about 4 carbon atoms and X$^-$ is as previously defined.

In still further embodiments of organomodified monosilyl compound $R^1$—Si(CH$_3$)$_2$—Z, $R^1$ contains from 2 to 4 methyl groups, $CR^1R^2R^3$ is (H$_3$C)$_2$CH— or (H$_3$C)$_3$C—, m is 0 or 1, n is 0, Z is $R^3$ and $R^3$ is —CH$_2$CH$_2$CH$_2$—O—CH(OH)—CH$_2$—N$^+$(CH$_3$)$_2$—$R^5$ [X$^-$] in which $R^5$ is a linear or branched alkyl group of from 1 to about 4 carbon atoms and X$^-$ is a carboxylate anion of from 2 to about 22 carbon atoms, preferably from 2 to about 10 carbon atoms and more preferably from 2 to 6 carbon atoms, optionally containing 1 or 2 hydroxyl groups.

In particular embodiments of the organomodified monosilyl compound herein, X$^-$ is the anion of: a monocarboxylic acid such as acetic acid, propionic acid or butyric acid; a dicarboxylic acid such as succinic acid, maleic acid or oxalic acid; a tricarboxylic acid; an alpha-hydroxy acid such as glycolic acid, lactic acid, citric acid or mandelic acid; a beta-hydroxy acid such as a hydroxypropionic acid, salicylic acid, carnitine, β-Hydroxy β-methylbutyric acid or 3-hydroxybutyric acid; a dihydroxy acid such as dimethylol propionic acid; or, a saturated or unsaturated fatty acid such as caprylic acid, capric acid, caproic acid, oleic acid, myristoleic acid, stearic acid, linoleic acid or erucic acid.

A. Method for Preparing the Organomodified Monosilyl Compound

Organomodified monosilyl compounds of the invention can be prepared by any of several synthesis processes the requirements of which are well known in the art.

According to one method of preparation of organomodified monosilyl compounds $R^1$—Si(CH$_3$)$_2$—Z of the invention, at least one branched alkene is reacted under catalytic hydrosilylation reaction conditions with dimethylsilylchloride to provide a chlorosilane adduct which is then made to undergo reduction to provide the corresponding silylhydride intermediate. Branched alkenes that are useful in preparing the foregoing chlorosilane adduct and silylhydride intermediate used in the preparation of organomodified monosilyl compounds $R^1$—Si(CH$_3$)$_2$—Z herein include, e.g., the following and mixtures thereof:

| | |
|---|---|
| (H$_3$C)$_2$CHCH$_2$CH=CH$_2$ | H$_3$CCH$_2$C(CH$_3$)CH=CH$_2$ |
| 4-methyl-1-pentene | 3-methyl-1-pentene |
| (H$_3$C)$_3$CCH=CH$_2$ | H$_3$CCH$_2$C(CH$_3$)$_2$CH=CH$_2$ |
| 3,3-dimethyl-1-butene | 3,3-dimethyl-1-pentene |
| (H$_3$C)$_2$CHCH=CH$_2$ | (H$_3$C)$_2$CHCH(CH$_3$)=CH$_2$ |
| 3-methyl-1-butene | 2,3-dimethyl-1-butene |
| (H$_3$C)$_2$CHC(CH$_3$)C(CH$_3$)=CH$_2$ | H$_3$CCH$_2$C(CH$_3$)$_2$C(CH$_2$) |
| 2,3,4-trimethyl-1-pentene | 2,3,3-trimethyl-1-pentene |
| H$_3$CCH$_2$C(CH$_3$)=CH$_2$ | (HC$_3$)$_3$CCH(CH$_3$)CH-CH$_2$ |
| 2-methyl-1-butene | 3,4,4-trimethyl-1-pentene |
| (H$_3$C)$_3$CC(CH$_3$)=CH$_2$ | H$_3$CCH$_2$CH$_2$CH(CH$_3$)=CH$_2$ |
| 2,3,3-trimethyl-1-butene | 2,4,4-trimethy1-1-butene |
| (H$_3$C)$_3$CCH$_2$CH=CH$_2$ | H$_3$CCH(CH$_3$)CH$_2$CH$_2$CH=CH$_2$ |
| 4,4-dimethyl-1-pentene | 5-methyl-1-hexene |
| (H$_3$C)$_3$CC(CH$_3$)=CH$_2$ | H$_3$CC(CH$_3$)$_2$CH$_2$CH$_2$CH=CH$_2$ |
| 2,3,3-trimethyl-1-butene | 5,5-dimethyl-1-hexene |

Reduction of the chlorosilane adduct, including mixtures thereof, to provide the silylhydride intermediate(s) can be conveniently carried out employing any of various metal complexes as is well known in the art, e.g., complexes of such metals as aluminum, lithium, nickel, palladium or platinum. Many types of aluminum catalysts for halosilane reduction are known and such complexes may be used to generate the hydride intermediate herein. In one embodiment, the metal complex is the organoaluminium compound sodium bis(2-methoxyethyl) aluminum hydride, commercially available as Vitride (Vertellus) or Red-Al (Sigma-Aldrich).

Reaction of the hydride intermediate(s) with one or more allyl- or methallyl-ethers or polyethers, e.g., of the general formula H$_2$C=CR$^{13}$CH$_2$—O—(C$_2$H$_4$O)$_a$(C$_3$H$_6$O)$_b$(C$_4$H$_8$O)$_c$—$R^4$, in which $R^4$ is hydrogen or methyl and $R^{13}$ and subscripts a, b and c are as previously defined, is carried out under catalytic hydrosilylation reaction conditions to provide ether/polyether-modified monosilyl compounds of the invention.

Suitable olefinically modified ethers/polyethers, including mixtures thereof, that may be reacted with the silyl hydride intermediate to provide ether/polyether-modified monosilyl compounds of the invention include allyl propyl ether, methallyl propyl ether, polyethyleneglycol allylether, polyethyleneglycol polypropyleneglycol allylether, polypropyleneglycol allyl ether, methoxy polyethyleneglycol allylether, methoxy polyethyleneglycol polypropyleneglycol allylether, butoxy polyethyleneglycol polyproplylene glycol allylether, methoxy polypropyleneglycol allylether, butoxy polypropyleneglycol allylether, polyethleneglycol polybutyleneglycol allylether, polyethyleneglycol polypropyleneglycol polybutyleneglycol allylether, and their mixtures. The allyl- and methallyl-terminated polyethers include those of the random and block types.

Hydrosilylation catalysts and their use are well known in the art and include complexes of such metals as rhodium, ruthenium, palladium, osmium, iridium and platinum. Many types of platinum-containing hydrosilylation catalyst can be used herein, e.g., those having the formula $PtCl_2$olefin and $HPtCl_3$olefin as described in U.S. Pat. No. 3,159,601, hereby incorporated by reference. Other platinum-containing hydrosilylation catalyst include complexes of chloroplatinic acid with up to 2 moles per gram of platinum and an alcohol, ether, aldehyde and mixtures thereof as described in U.S. Pat. No. 3,220,972, hereby incorporated by reference. Additional platinum-containing hydrosilylation catalysts useful in preparing the organomodified silylated compounds of the present invention are described in U.S. Pat. Nos. 3,715,334, 3,775,452 and 3,814,730 (Karstedt's catalyst), hereby incorporated by reference. Further background concerning hydrosilylation may be found in J. L. Spier, "Homogeneous Catalysis of Hydrosilylation by "Transition Metals", in Advances in Organometallic Chemistry, volume 17, pages 407 through 447, F. G. A. Stone and R. West editors, published by Academic Press (New York, 1979), hereby incorporated by reference. Those skilled in the art can readily determine the effective amount of catalyst for a given hydrosilylation reaction. Generally, an amount of hydrosilylation catalyst ranging from about 0.1 to 50 parts per million by weight of the desired hydrosilylation will be satisfactory.

Illustrated for 3,3-dimethyl-but-1-ene, one process for preparing ether/polyether-modified monosilyl compounds of the invention can be considered to proceed as follows:

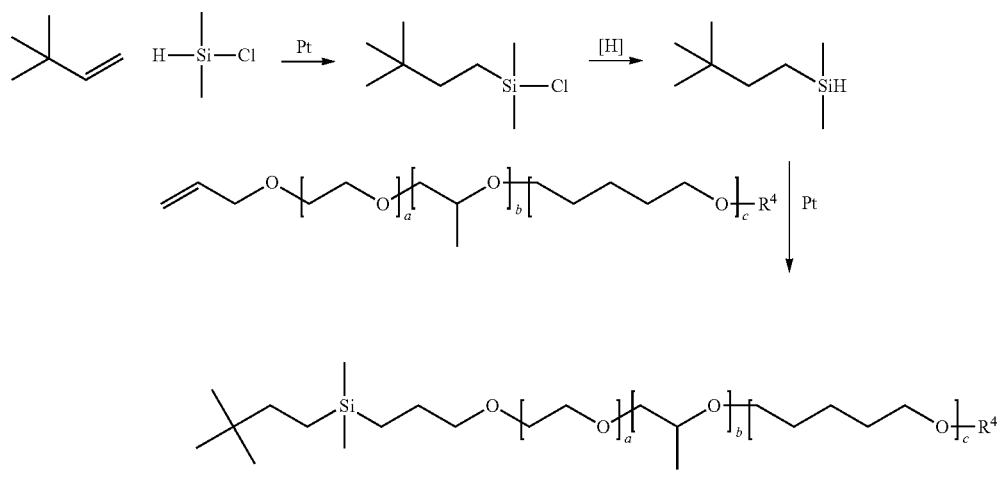

a + b + c = 1 to 20

The following ether/polyether-modified monosilyl compounds of the invention may be prepared in accordance with the synthesis described above:

| $CR^6R^7R^8(CR^9R^{10})_m(CR^{11}R^{12})_n$—$CHR^{13}$—$CH_2$—$Si(CH_3)_2$— | —Z |
|---|---|
| $(H_3C)_2CHCH_2CH_2$—$Si(CH_3)_2$— | —$CH_2CH_2CH_2$—O—$(C_2H_4O)_{7.5}$H |
| $(H_3C)_3CCH_2CH_2$—$Si(CH_3)_2$— | —$CH_2CH_2CH_2$—O—$(C_2H_4O)_{7.5}CH_3$ |
| $(H_3C)_2CHCH_2CH_2$—$Si(CH_3)_2$— | —$CH_2CH_2CH_2$—O$(CH_2H_4O)_5(C_3H_6O)_{2.5}$H |
| $(CH_3)_2CHCH(CH_3)CH(CH_3)CH_2$—$Si(CH_3)_2$— | —$CH_2CH_2CH_2$—O—$(CH_2CH_2O)_4$H |
| $H_3CCH_2CH(CH_3)CH_2CH_2$—$Si(CH_3)_2$— | —$CH_2CH_2CH_2$—O—$(C_2H_4O)_{7.5}$H |
| $H_3CCH_2C(CH_3)_2CH_2CH_2$—$Si(CH_3)_2$— | —$CH_2CH_2CH_2$—O—$(C_2H_4O)_{7.5}$H |
| $(H_3C)_2CHCH(CH_3)CH_2$—$Si(CH_3)_2$— | —$CH_2CH_2CH_2$—O—$(C_2H_4O)_{7.5}CH_3$ |
| $H_3CCH_2C(CH_3)_2C(CH_3)CH_2$—$Si(CH_3)_2$— | —$CH_2CH_2CH_2$—O$(CH_2H_4O)_5(C_3H_6O)_{2.5}$H |
| $(H_3C)_2CHCH_2CH_2CH_2$—$Si(CH_3)_2$— | —$CH_2CH_2CH_2$—O—$(CH_2CH_2O)_5$H |
| $(H_3C)_3CCH_2CH_2$—$Si(CH_3)_2$— | —$CH_2CH_2CH_2$—O—$CH_2CH_2OH$ |
| $(H_3C)_2CHCH(CH_3)CH_2$—$Si(CH_3)_2$— | —$CH_2CH_2CH_2$—O—$(C_2H_4O)_{7.5}$H |
| $(H_3C)_3CCH_2CH_2$—$Si(CH_3)_2$— | —$CH_2CH_2CH_2$—O$(CH_2H_4O)_5(C_3H_6O)_{2.5}$H |

According to another process for preparing organomodified monosilyl compounds $R^1$—$Si(CH_3)_2$—Z, specifically, one which provides quaternary-modified monosilyl compounds of the invention, the silyl hydride intermediate obtained as shown above is reacted with glycidyl ether and/or methallyl glycidyl ether followed by ring-opening reaction with a quaternary alkyldimethyl ammonium salt or quat-forming mixture of the desired acid X and tertiary alkyldimethylamine as illustrated by the reaction scheme:

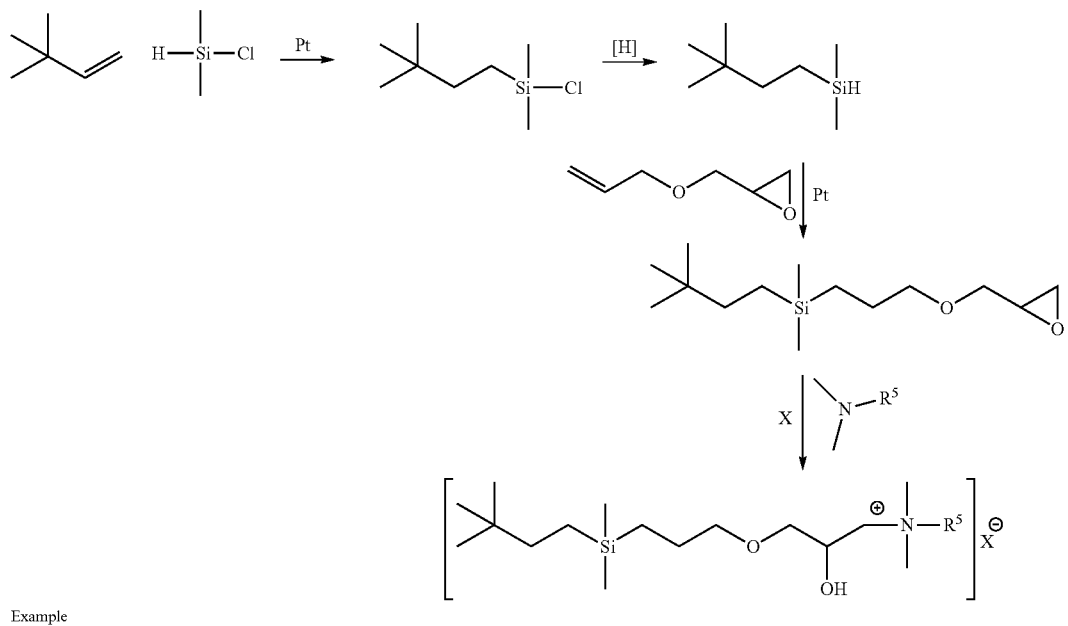

Example

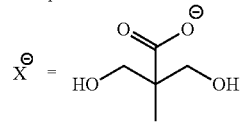

The following quaternary ammonium-modified monosilyl compounds $R^1$—Si(CH$_3$)$_2$—Z of the invention may be prepared in accordance with the synthesis described above:

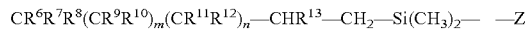

| CR$^6$R$^7$R$^8$(CR$^9$R$^{10}$)$_m$(CR$^{11}$R$^{12}$)$_n$—CHR$^{13}$—CH$_2$—Si(CH$_3$)$_2$— | —Z |
|---|---|
| (H$_3$C)$_2$CHCH$_2$CH$_2$CH$_2$—Si(CH$_3$)$_2$— | —CH$_2$CH$_2$CH$_2$—O—CH(OH)CH$_2$N$^+$(CH$_3$)$_2$—CH$_2$CH$_3$[CH$_3$CH$_2$COO$^-$] |
| (H$_3$C)$_2$CHCH(CH$_3$)CH$_2$—Si(CH$_3$)$_2$— | —CH$_2$CH$_2$CH$_2$—O—CH(OH)CH$_2$N$^+$(CH$_3$)$_2$—CH$_2$CH$_3$[CH$_3$CH$_2$COO$^-$] |
| H$_3$CCH$_2$C(CH$_3$)$_2$C(CH$_3$)CH$_2$—Si(CH$_3$)$_2$— | —CH$_2$CH$_2$CH$_2$—O—CH(OH)CH$_2$N$^+$(CH$_3$)$_2$—CH$_2$CH$_3$R[(CH$_2$OH)$_2$(CH$_3$)C—COO$^-$] |
| (H$_3$C)$_3$CCH$_2$CH$_2$—Si(CH$_3$)$_2$— | —CH$_2$CH$_2$CH$_2$—O—CH(OH)CH$_2$N$^+$(CH$_3$)$_2$—CH$_2$CH$_3$[(CH$_2$OH)$_2$(CH$_3$)C—COO$^-$] |

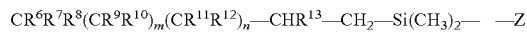

| CR$^6$R$^7$R$^8$(CR$^9$R$^{10}$)$_m$(CR$^{11}$R$^{12}$)$_n$—CHR$^{13}$—CH$_2$—Si(CH$_3$)$_2$— | —Z |
|---|---|
| (H$_3$C)$_3$CCH$_2$CH$_2$—Si(CH$_3$)$_2$— | —CH$_2$CH$_2$CH$_2$—O—CH$_2$CH(OH)CH$_2$N$^+$(CH$_3$)$_2$—CH$_2$CH$_2$CH$_2$OH[(CH$_2$OH)$_2$(CH$_3$)C—COO$^-$] |
| (H$_3$C)$_2$CHCH$_2$CH$_2$—Si(CH$_3$)$_2$— | —CH$_2$CH$_2$CH$_2$—O—CH(OH)CH$_2$N$^+$(CH$_3$)$_2$—CH$_2$CH$_3$ [CH$_3$CH$_2$COO$^-$] |
| (H$_3$C)$_2$CHCH(CH$_3$)CH(CH$_3$)CH$_2$—Si(CH$_3$)$_2$— | —CH$_2$CH$_2$CH$_2$—O—CH(OH)CH$_2$N$^+$(CH$_3$)$_2$—CH$_2$CH$_3$ [CH$_2$(OH)CH$_2$COO$^-$] |
| H$_3$CCH$_2$CH(CH$_3$)CH$_2$CH$_2$—Si(CH$_3$)$_2$— | —CH$_2$CH$_2$CH$_2$—O—CH(OH)CH$_2$N$^+$(CH$_3$)$_2$—CH$_2$CH$_3$ [CH$_2$(OH)CH$_2$COO$^-$] |
| H$_3$CCH$_2$C(CH$_3$)$_2$CH$_2$CH$_2$—Si(CH$_3$)$_2$— | —CH$_2$CH$_2$CH$_2$—O—CH(OH)CH$_2$N$^+$(CH$_3$)$_2$—CH$_2$CH$_3$ [CH$_2$(OH)CH$_2$COO$^-$] |
| (H$_3$C)$_2$CHCH$_2$CH$_2$—Si(CH$_3$)$_2$— | —CH$_2$CH$_2$CH$_2$—O—CH(OH)CH$_2$N$^+$(CH$_3$)$_2$—CH$_2$CH$_3$ [CH$_2$(OH)CH$_2$CH$_2$COO$^-$] |
| H$_3$CC(CH$_3$)$_2$CH$_2$CH$_2$CH$_2$—CH$_2$—Si(CH$_3$)$_2$— | —CH$_2$CH$_2$CH$_2$—O—CH(OH)CH$_2$N$^+$(CH$_3$)$_2$—CH$_2$CH$_3$ [CH$_2$(OH)CH$_2$COO$^-$] |

B. Compositions Containing Organomodified Monosilyl Compound $R^1$—Si(CH$_3$)$_2$—Z The organomodified monosilyl compound of the present invention may be utilized in a variety of forms: as liquid solutions, dispersions of solids in liquids, dispersions of liquids in liquids, solid mixtures or solid solutions, etc., either separately or in combinations thereof. Compositions will generally contain a wetting agent-effective amount of one or more organomodified silyl compounds $R^1$—Si(CH$_3$)$_2$—Z of the invention, e.g., depending on the particular purpose or use of a given composition, from about 0.01 to about 99, and advantageously from about 0.1 to about 50 weight percent of the organomodified silyl compound(s) based on the weight of the composition.

1. Agrochemical Compositions

Many pesticide applications require the addition of an adjuvant to the spray mixture to provide wetting and spreading on foliar surfaces. Often that adjuvant is a surfactant, which can perform a variety of functions, such as increasing spray droplet retention on difficult to wet leaf surfaces, enhance spreading to improve spray coverage, or to provide penetration of the herbicide into the plant cuticle. These adjuvants are provided either as a tank-side additive or used as a component in pesticide formulations.

Typical uses for pesticides include agricultural, horticultural, turf, ornamental, home and garden, veterinary and forestry applications. The pesticidal compositions of the present invention also include at least one pesticide, where the quaternary organosilicon surfactant of the present invention is present at an amount sufficient to deliver between 0.005 and 2 weight percent pesticide to the final use concentration, either as a concentrate or diluted in a tank mix. Optionally the pesticidal composition may include excipients, cosurfactants, solvents, foam control agents, deposition aids, drift retardants, biologicals, micronutrients, fertilizers and the like. The term pesticide means any compound used to destroy pests, e.g., rodenticides, insecticides, miticides, fungicides, and herbicides. Illustrative examples of pesticides that can be employed include, but are not limited to, growth regulators, photosynthesis inhibitors, pigment inhibitors, mitotic disrupters, lipid biosynthesis inhibitors, cell wall inhibitors, and cell membrane disrupters. The amount of pesticide employed in compositions of the invention varies with the type of pesticide employed. More specific examples of pesticide compounds that can be used with the compositions of the invention are, but not limited to, herbicides and growth regulators, such as: phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, sulfonylureas, imidazolinones, clethodim, diclofop-methyl, fenoxaprop-ethyl, fluazifop-p-butyl, haloxyfop-methyl, quizalofop, sethoxydim, dichlobenil, isoxaben, and bipyridylium compounds.

Fungicide compositions that can be used with the present invention include, but are not limited to, aldimorph, tridemorph, dodemorph, dimethomorph; flusilazol, azaconazole, cyproconazole, epoxiconazole, furconazole, propiconazole, tebuconazole and the like; imazalil, thiophanate, benomyl carbendazim, chlorothialonil, dicloran, trifloxystrobin, fluoxystrobin, dimoxystrobin, azoxystrobin, furcaranil, prochloraz, flusulfamide, famoxadone, captan, maneb, mancozeb, dodicin, dodine, and metalaxyl.

Insecticides, including larvacide, miticide and ovacide compounds that can be used with the composition of the present invention, but not limited to, Bacillus thuringiensis, spinosad, abamectin, doramectin, lepimeectin, pyrethrins, carbaryl, primicarb, aldicarb, methomyl, amitraz, boric acid, chlordimeform, novaluron, bistrifluron, triflumuron, diflubenzuron, imidacloprid, diazinon, acephate, endosulfan, kelevan, dimethoate, azinphos-ethyl, azinphos-methyl, izoxathion, chlorpyrifos, clofentezine, lambda-cyhalothrin, permethrin, bifenthrin, cypermethrin and the like.

2. Fertilizers and Micronutrients

Fertilizers or micronutrients include, but not limited to, zinc sulfate, ferrous sulfate, ammonium sulfate, urea, urea ammonium nitrogen, ammonium thiosulfate, potassium sulfate, monoammonium phosphate, urea phosphate, calcium nitrate, boric acid, potassium and sodium salts of boric acid, phosphoric acid, magnesium hydroxide, manganese carbonate, calcium polysulfide, copper sulfate, manganese sulfate, iron sulfate, calcium sulfate, sodium molybdate, calcium chloride.

The fertilizer or micronutrient may be a liquid or a solid. If a solid, it is preferable that it is soluble in a solvent, or the quaternary organosilicon surfactant of the present invention, prior to application, and the silicone may act as a solvent, or surfactant for such solubility or additional surfactants may perform this function.

3. Agricultural Excipients

Buffers, preservatives and other standard agricultural excipients known in the art also may be included in a composition of the invention.

Solvents may also be included in compositions of the present invention. These solvents are in a liquid state at room temperature. Examples include water, alcohols, aromatic solvents, oils (i.e. mineral oil, vegetable oil, silicone oil, and so forth), lower alkyl esters of vegetable oils, fatty acids, ketones, glycols, polyethylene glycols, diols, paraffinics, and so forth. Particular solvents would be 2, 2, 4 trimethyl, 1 3 pentane diol and alkoxylated (especially ethoxylated) versions thereof as illustrated in U.S. Pat. No. 5,674,832, herein incorporated by reference, or N-methyl-pyrrolidone.

4. Cosurfactants

Cosurfactants useful in the compositions herein include nonionic, cationic, anionic, amphoteric, zwitterionic, polymeric surfactants, or any mixture thereof. Surfactants are typically hydrocarbon based, silicone based or fluorocarbon based.

Moreover, other cosurfactants, that have short chain hydrophobes that do not interfere with superspreading as described in U.S. Pat. No. 5,558,806 herein incorporated by reference are also useful.

Useful surfactants include alkoxylates, especially ethoxylates, containing block copolymers including copolymers of ethylene oxide, propylene oxide, butylene oxide, and mixtures thereof; alkylarylalkoxylates, especially ethoxylates or propoxylates and their derivatives including alkyl phenol ethoxylate; arylarylalkoxylates, especially ethoxylates or propoxylates. and their derivatives; amine alkoxylates, especially amine ethoxylates; fatty acid alkoxylates; fatty alcohol alkoxylates; alkyl sulfonates; alkyl benzene and alkyl naphthalene sulfonates; sulfated fatty alcohols, amines or acid amides; acid esters of sodium isethionate; esters of sodium sulfosuccinate; sulfated or sulfonated fatty acid esters; petroleum sulfonates; N-acyl sarcosinates; alkyl polyglycosides; alkyl ethoxylated amines; and so forth.

Specific examples include alkyl acetylenic diols (SURFONYL—Air Products), pyrrilodone based surfactants (e.g., SURFADONE—LP 100—Ashland), 2-ethyl hexyl sulfate, isodecyl alcohol ethoxylates (e.g., RHODASURF DA 530—Rhodia), ethylene diamine alkoxylates (TETRONICS—BASF), ethylene oxide/propylene oxide copolymers (PLURONICS—BASF), Gemini type surfactants (Rhodia) and diphenyl ether Gemini type surfactants (e.g. DOWFAX—Dow Chemical).

Preferred surfactants include ethylene oxide/propylene oxide copolymers (EO/PO); amine ethoxylates; alkyl polyglycosides; oxo-tridecyl alcohol ethoxylates, and so forth.

In a preferred embodiment, the agrochemical composition of the present invention further comprises one or more agrochemical ingredients. Suitable agrochemical ingredients include, but not limited to, herbicides, insecticides, growth regulators, fungicides, miticides, acaricides, fertilizers, biologicals, plant nutritionals, micronutrients, biocides, paraffinic mineral oil, methylated seed oils (i.e. methylsoyate or methylcanolate), vegetable oils (such as soybean oil and canola oil), water conditioning agents such as Choice® (Loveland Industries, Greeley, Colo.) and Quest® (Helena Chemical, Collierville, Tenn.), modified clays such as Surround® (BASF), foam control agents, surfactants, wetting agents, dispersants, emulsifiers, deposition aids, antidrift components, and water.

Suitable agrochemical compositions are made by combining, in a manner known in the art, such as, by mixing one or more of the above components with the quaternary organosilicon surfactant of the present invention, either as a tank-mix, or as an "In-can" formulation. The term "tank-mix" means the addition of at least one agrochemical to a spray medium, such as water or oil, at the point of use. The term "In-can" refers to a formulation or concentrate containing at least one agrochemical component. The "In-can" formulation may then diluted to use concentration at the point of use, typically in a Tank-mix, or it may be used undiluted.

5. Coating Compositions

Typically, coating formulations require a wetting agent or surfactant for the purpose of emulsification, compatibilization of components, leveling, flow and reduction of surface defects. Additionally, these additives may provide improvements in the cured or dry film, such as improved abrasion resistance, antiblocking, hydrophilic, and hydrophobic properties. Coatings formulations may exist as, Solvent-borne coatings, water-borne coatings and powder coatings.

The coatings components may be employed as: architecture coatings; OEM product coatings such as automotive coatings and coil coatings; Special Purpose coatings such as industrial maintenance coatings and marine coatings;

Typical resin types include: polyesters, alkyds, acrylics, epoxies and polyurethanes.

6. Personal Care Products

In a preferred embodiment, the quaternary organosilicon surfactant of the present invention comprises, per 100 parts by weight ("pbw") of the personal care composition, from 0.1 to 99 pbw, more preferably from 0.5 pbw to 30 pbw and still more preferably from 1 to 15 pbw of the quaternary organosilicon surfactant and from 1 pbw to 99.9 pbw, more preferably from 70 pbw to 99.5 pbw, and still more preferably from 85 pbw to 99 pbw of the personal care composition.

The silylated surfactant compositions of the present invention may be utilized in personal care emulsions, such as shampoo and conditioners as well as lotions, and creams.

The personal care applications where the silylated surfactant compositions of the present invention and the silicone compositions derived therefrom of the present invention may be employed include, but are not limited to, deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products such as nail polish, nail polish remover, nails creams and lotions, cuticle softeners, protective creams such as sunscreen, insect repellent and anti-aging products, color cosmetics such as lipsticks, foundations, face powders, eye liners, eye shadows, blushes, makeup, mascaras and other personal care formulations where silicone components have been conventionally added, as well as drug delivery systems for topical application of medicinal compositions that are to be applied to the skin.

In a preferred embodiment, the personal care composition of the present invention further comprises one or more personal care ingredients. Suitable personal care ingredients include, for example, emollients, moisturizers, humectants, pigments, including pearlescent pigments such as, for example, bismuth oxychloride and titanium dioxide coated mica, colorants, fragrances, biocides, preservatives, antioxidants, anti-microbial agents, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, volatile silicones, organic oils, waxes, film formers, thickening agents such as, for example, fumed silica or hydrated silica, particulate fillers, such as for example, talc, kaolin, starch, modified starch, mica, nylon, clays, such as, for example, bentonite and organomodified clays.

Suitable personal care compositions are made by combining, in a manner known in the art, such as, for example, by mixing, one or more of the above components with the silylated surfactant compositions. Suitable personal care compositions may be in the form of a single phase or in the form of an emulsion, including oil-in-water, water-in-oil and anhydrous emulsions where the silicone phase may be either the discontinuous phase or the continuous phase, as well as multiple emulsions, such as, for example, oil-in water-in-oil emulsions and water-in-oil-in water-emulsions.

In another useful embodiment, a skin care composition comprises the silylated surfactant compositions of the present invention, and a vehicle, such as, for example, a silicone oil or an organic oil. The skin care composition may, optionally, further include emollients, such as, for example, triglyceride esters, wax esters, alkyl or alkenyl esters of fatty acids or polyhydric alcohol esters and one or more the known components conventionally used in skin care compositions, such as, for example, pigments, vitamins, such as, for example, Vitamin A, Vitamin C and Vitamin E, sunscreen or sunblock compounds, such as, for example, titanium dioxide, zinc oxide, oxybenzone, octylmethoxy cinnamate, butylmethoxy dibenzoylmethane, p-aminobenzoic acid and octyl dimethyl-p-aminobenzoic acid.

In another useful embodiment, a color cosmetic composition, such as, for example, a lipstick, a makeup or a mascara composition comprises the silylated surfactant composition, and a coloring agent, such as a pigment, a water soluble dye or a liposoluble dye.

The uses of the compositions of the present invention are not restricted to personal care compositions, other products such as waxes, polishes and textiles treated with the compositions of the present invention are also contemplated.

7. Home Care Products

Home care applications include laundry detergent and fabric softener, dishwashing liquids, wood and furniture polish, floor polish, tub and tile cleaners, toilet bowl cleaners, hard surface cleaners, window cleaners, antifog agents, drain cleaners, auto-dish washing detergents and sheeting agents, carpet cleaners, prewash spotters, rust cleaners and scale removers.

The following examples are illustrative of the organomodified silylated surfactant of the invention, its preparation, its properties, and its use in a herbicide composition.

Example 1: Preparation of Chlorosilane Adduct

A 2000 mL four-neck round bottom flask was equipped with a magnetic stir bar, reflux condenser with nitrogen gas inlet, thermocouple, addition funnel and heating mantle. 3,3-Dimethyl-1-butene (170.69 g, 2.02 mol, 99.6 weight percent purity) and Karstedt's catalyst (5 ppm) were charged to the flask, at 15° C. under N₂. The flask was warmed up to 35° C. dimethylsilyl chloride (192.08 g, 2 mol, 98.5 weight percent purity) was charged to the addition funnel, and added drop wise to the round bottom flask. An immediate exotherm was noted. Addition of dimethylsilyl chloride was continued over 2.5 hours. After addition, the reaction was maintained at 40° C. for 3 hours, and then analyzed by gas chromatography. Found: >95 percent conversion to chlorosilane adduct.

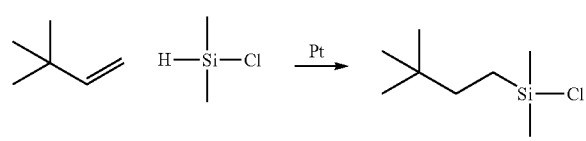

Example 2: Preparation of Hydride Intermediate

The chlorosilane adduct of Example 1 was cooled to 1° C. A solution of sodium dihydro-bis-(2-methoxyethoxy) aluminate (Vitride, 61.8 weight percent in toluene; 359.83 g of solution, 1.1 mol) was charged to an addition funnel and added drop wise to the solution of chlorosilane at a rate to maintain reaction temperature <5° C. (total addition time ~3.5 hours). After completion of addition, reaction mixture was stirred and slowly allowed to warm to room temperature (~12 hours). Finally, to this reaction mixture, 275 g of diethylene glycol dibutyl ether was added and stripped under vacuum. The clear colorless product was collected as a 50 weight percent solution in toluene. Product was analyzed by gas chromatography and found to have undergone quantitative conversion to the desired reduction product.

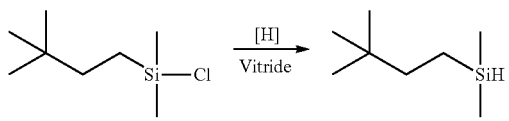

Examples 3-7; Comparative Examples 1-3: Preparation of Organomodified Monosilyl Compounds The hydride intermediate of Example 2 was farther modified with various allyl polyalkyleneoxides to produce organomodified monosilyl compounds of the present invention (Table 1) as well as several compounds outside the scope of the invention for purposes of comparison (Table 2).

The organomodified monosilyl compounds of the present invention as well as those prepared for comparison purposes were obtained by conventional methods of platinum-mediated hydrosilylation, e.g., as described in Bailey, U.S. Pat. No. 3,299,112, herein incorporated by reference. A representative synthesis is set forth below.

A 100 mL round bottom flask was equipped with a magnetic stir bar, reflux condenser with nitrogen inlet, thermocouple, addition funnel and heating mantle. Allyl polyether with an avg. molecular weight of about 350 g/mol (3.5 g; 0.01 mol), chloroplatinic acid (5 ppm) and sodium propionate (3.5 mg) were charged to the round bottom flask, stirred and brought to 85° C. The solution of carbosilane (Example 2) in toluene (15 g of 8 weight percent solution; 0.00833 mol carbosilane) was charged to the addition funnel and added drop wise to the flask. An immediate exotherm was noted, addition was continued over 45 minutes. After complete addition, the reaction was maintained at 85° C. for 5 hours. The reaction product was tested for Si—H content and indicated 0 cc H₂/g remaining. The reaction mixture was stripped (~10 mm Hg, 100° C.) for 1.5 hours to remove volatiles, allowed to cool to <40° C., treated with celite and sodium bicarbonate, stirred, pressure-filtered, and bottled. Yield: 4 g of clear, brown color liquid.

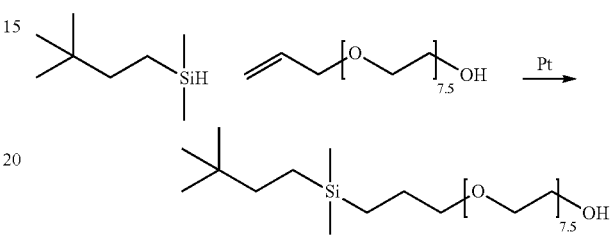

Table 1 below lists polyether-modified monosilyl compounds of the present invention conforming to the general structure:

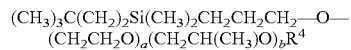

$(CH_3)_3C(CH_2)_2Si(CH_3)_2CH_2CH_2CH_2—O—$
$(CH_2CH_2O)_a(CH_2CH(CH_3)O)_bR^4$ wherein subscripts a and b and group $R^4$ are as set forth therein.

TABLE 1

| Compounds of the Invention | | | |
|---|---|---|---|
| Compound | subscript a | subscript b | $R^4$ |
| Ex. 3 | 7.5 | 0 | $CH_3$ |
| Ex. 4 | 7.5 | 0 | H |
| Ex. 5 | 4 | 0 | H |
| Ex. 6 | 11 | 0 | H |
| Ex. 7 | 5 | 2.5 | H |

Table 2 lists three organomodified monosilyl compounds outside the scope of the present invention and conforming to the general structure:

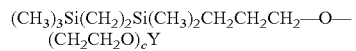

$(CH_3)_3Si(CH_2)_2Si(CH_3)_2CH_2CH_2CH_2—O—$
$(CH_2CH_2O)_cY$ wherein subscript b and group Y are as set forth therein. Each of the compounds of Comparative Examples 1-3 differs from those of the invention in the nature of the alkyl group bonded to the silicon atom, specifically, in having only 4 carbon atoms in the alkyl group compared to the compounds of the invention which must contain at least 5, and up to 8, carbon atoms in the alkyl group.

TABLE 2

| Comparative Organomodified Monosilyl Compounds | | |
|---|---|---|
| Compound | subscript c | Y |
| Comp. Ex. 1 | 7.5 | $CH_3$ |
| Comp. Ex. 2 | 7.5 | H |
| Comp. Ex. 3 | 11 | H |

Example 8: Preparation of Quaternary-Modified Monosilyl Compound (QC-1)

The following reaction scheme shows the preparation of a quaternary-modified monosilyl compound employing known and conventional synthesis procedures:

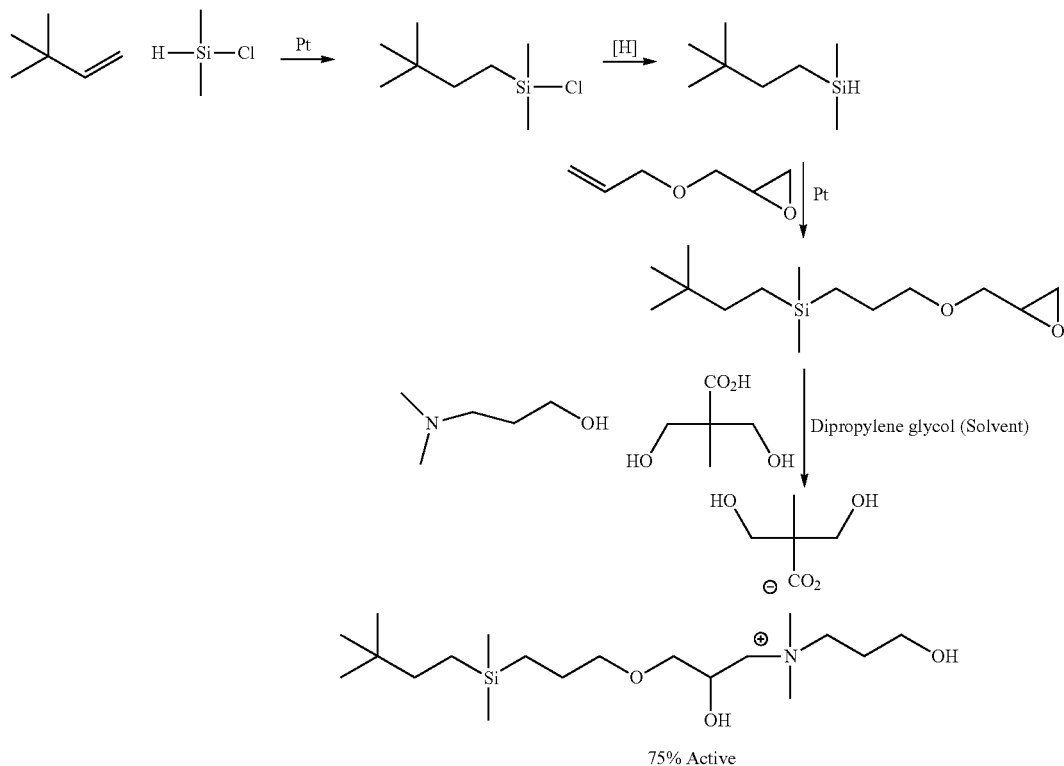

75% Active 26 g (0.1 mol) of the monoepoxy-functional monosilyl compound shown above, 10.39 g (0.1 mol) of N, N'-dimethylamino propanol, 13.86 g (0.1 mol) of dimethylol propionic acid and 16.75 g (0.1 mol) of dipropylene glycol solvent were charged into a 3-neck flask provided with a condenser and nitrogen blanket. The mixture was quickly heated to 80-82° C. and continuously stirred for 18 hours. The flask was thereafter cooled to room temperature to obtain a brown color viscous solution of the above indicated mentioned quaternary ammonium-modified monosilyl compound $(H_3C)_3CCH_2CH_2-Si(CH_3)_2-CH_2CH_2CH_2-O-CH_2CH(OH)CH_2N^+(CH_3)_2-CH_2CH_2CH_2OH$ $[(CH_2OH)_2(CH_3)C-COO^-]$ at 75 wt % in dipropylene glycol.

Example 9: Spreading Properties of Organomodified Monosilyl Compounds $R^1-Si(CH_3)_2-Z$ Spreading was determined by applying a 10 μL droplet, of surfactant solution to polystyrene Petri dishes (Fisher Scientific) and measuring the spread diameter (mm) after 30 seconds, at a relative humidity between 50 and 70% (at 22 to 25° C.). The solution was applied with an automatic pipette to provide droplets of reproducible volume. Deionized water that was further purified with a Millipore filtration system was used to prepare the surfactant solutions.

Table 3 demonstrates that the compounds of the present invention (Examples 3-8) provide spreading properties similar to the comparative compounds (Comparative Examples 1-3). Additionally, as the polyethylene content increases from about 4 EO to 7.5 EO to 11 EO unites (compare results of Example 6 with Example 2), there was a corresponding increase in spreading for the compounds of the present invention,

TABLE 3

Spreading Properties of Compounds

| Compound | Spread Diameter (mm); Weight % Compound | | |
|---|---|---|---|
| | 0.05% | 0.1% | 0.2% |
| Ex. 3 | 31 | 48 | 50 |
| Ex. 4 | 29 | 46 | 48 |
| Ex. 5 | 23 | 23 | 23 |
| Ex. 6 | 6 | 7 | 7 |
| Ex. 7 | 34 | 49 | 47 |
| Ex. 8 | 10 | 21 | 33 |
| Comp. Ex. 1 | 27 | 38 | 46 |
| Comp. Ex. 2 | 30 | 39 | 44 |

Example 10: Hydrolytic Stability of the Organomodified Monosilylated Compound Hydrolytic stability was determined for a representative compound of the present invention using spreading as an indicator of stability. It is well known that hydrolysis of organosilicon surfactants significantly decreases over time when exposed to a low pH environment, e.g., pH of 3.

Spreading was determined according to the method described in Example 1. Surfactant solutions were prepared in either deionized water (~pH 5) and in a pH 3 buffer solution (Fischer Scientific).

Table 4 demonstrates that the organomodified monosilyl compounds of the present invention are resistant to hydrolysis at pH 3 and pH 4. Spreading was essentially unchanged over the test period.

TABLE 4

Effect of pH on Hydrolysis Stability of Organomodified Silyl Compounds

| Compound | Initial | 24h | 5d | 30d | 90d |
|---|---|---|---|---|---|
| Comp. Ex. 1 | 55 | 52 | 49 | nd | nd |
| Comp. Ex. 1 in pH 3 buffer | 49 | 45 | 42 | nd | 42 |
| Ex. 4 | 41 | 46 | 41 | nd | nd |
| Ex. 4 in pH 3 buffer | 44 | 39 | 37 | 47 | 47 |
| Ex. 4 in pH 4 buffer | 45 | nd | nd | 47 | 46 |

Example 11: Uptake of 2,4-D-Dimethylamine Salt into Canola Leaf

The uptake of $[C^{14}]$-2,4-dichlorophenoxyacetic acid, dimethylamine salt (2,4-D DMA salt) (1% a.e./100 L/ha) was determined in canola at 2 HAT and 24 HAT (Hours After Treatment) according to the method described by Lui, in Pro. 18th Asian-Pacific Weed Sci. Soc. Conf., pp. 561-566. Liu, Z Q; 2001.

Table 6 demonstrates that the organomodified monosilyl compounds of the present invention show equivalent or improved uptake of 2,4-D dimethylamine into canola leaf relative to the compound of Comparative Example 1.

TABLE 6

Uptake of $[C^{14}]$-2,4-D, DMA Salt Into Canola Leaf

| Compound | % wt/vol | Uptake % (2 HAT) | Uptake % (24 HAT) |
|---|---|---|---|
| Ex. 3 | 0.1% | 25.3 d | 63.4 abc |
| Ex. 2 | 0.1% | 27.4 d | 64.2 ab |
| Ex. 7 | 0.1% | 23.7 d | 54.4 c |
| Comp. Ex. 1 | 0.1% | 27.8 d | 63.8 ab |
| Ex. 3 | 0.15% | 23.4 d | 68.5 ab |
| Ex. 4 | 0.15% | 28.5 d | 65.8 ab |
| Ex. 7 | 0.15% | 22.5 de | 65.7 ab |
| Comp. Ex. 1 | 0.15% | 25.5 d | 59.9 be |

Means sharing common postscripts are not significantly different (p = 0.05).

Example 12: Effect of Spray Droplet Adhesion on Total Available Dose on Canola Leaf A spray droplet was generated by a dynamic system via a spray nozzle. The addition of a compound to a spray mixture can help reduce surface tension allowing the droplets to adhere to the target leaf. However, not all compounds promote the same level of droplet adhesion and therefore only a portion of the spray adheres to the leaf. The remaining spray may bounce off the leaf making it ineffective for delivery of the desired agrochemical (i.e. herbicide, fungicide, fertilizer, etc.).

The Total Available Dose (TAD) takes into consideration both agrochemical uptake and spray droplet adhesion. The TAD is the amount of material delivered to a plant surface (Adhesion) that is available for Uptake in to the foliage. Essentially TAD=Uptake (%)×Droplet Adhesion (%). The higher the TAD the higher the uptake potential.

Spray droplet adhesion (as a % of impacted droplets) was determined as described previously (Stevens et al. 1993) using a piezoelectric droplet generator with a 200 μm nozzle orifice to form mono-sized droplets of approx. 450 μm. The droplet freefall distance was 53 cm. Canola foliage (difficult-to-wet) was used as the impaction surface, with a leaf angle of 22.5°.

Solutions (0.15%) of the compounds of the present invention and that of Comparative Example 1 were prepared using deionized water. Solutions also contained 2,4-D DMA salt (1%) as the herbicide.

Determination of the TAD used the uptake results from the previous example (Table 7) along with the adhesion results reported in Table 6.

Table 7 below demonstrates that the organomodified monosilyl compounds of the present invention provided similar or better droplet adhesion on canola leaf relative to the comparative compound. However, the compounds of the present invention provide a higher TAD than the compound of Comparative Example 1.

TABLE 7

Effect of Droplet Adhesion on Total Available Dose of 2,4-D DMA Into Canola Leaf

| Compound | % wt/vol | Uptake % (2 HAT) | Uptake % (24 HAT) | Droplet Adhesion (%) | TAD (2 HAT) | TAD (24 HAT) |
|---|---|---|---|---|---|---|
| None (2,4-D alone) | 0 | 12.1e | 70.2 a | 7.0 | 0.8 | 4.9 |
| Ex. 3 | 0.15% | 23.4d | 68.5 ab | 97 | 22.7 | 66.4 |
| Ex, 4 | 0.15% | 28.5d | 65.8 ab | 93 | 26.5 | 61.1 |
| Ex. 7 | 0.15% | 22.5de | 65.7 ab | 91 | 2.8 | 63.7 |
| Comp. Ex. 1 | 0.15% | 25.5d | 59.9 be | 93 | 23.7 | 55.7 |

Means sharing common postscripts are not significantly different (p = 0.05)

While the invention has been described with reference to particular embodiments, those skilled in the art will understand that various changes may be made and equivalents may be substituted for elements thereof without departing from the scope of the invention. It is intended that the invention not be limited to the particular embodiments disclosed but that it include all embodiments falling within the scope of the appended claims.

The invention claimed is:

1. An organomodified monosilyl compound of the general formula:

$$R^1\text{—Si(CH}_3\text{)}_2\text{—Z}$$

wherein:
$R^1$ is a branched monovalent hydrocarbon group of from 5 to 8 carbon atoms containing at least two methyl groups;
Z is $R^2$ or $R^3$;
—$R^2$ is $CH_2CH_2CH_2\text{—O—(}C_2H_4\text{—O)}_a(C_3H_6O)_b(C_4H_8O)_c\text{—}R^4$ in which $R^4$ is hydrogen, a linear or branched monovalent hydrocarbon group of from 1 to about 4 carbon atoms or an acyl group, subscript a is from 1 to about 20, subscript b is from 0 to about 19, subscript c is from 0 to about 19 and the sum of subscripts a, b and c is from 1 to about 20; and,
$R^3$ is —$CH_2CH_2CH_2$—O—CH(OH)$CH_2$—$N^+(CH_3)_2$—$R^5$ [$X^-$] in which $R^5$ is a linear or branched hydrocarbon group of from 1 to about 4 carbon atoms or an acetyl group and $X^-$ is a saturated or unsaturated carboxylate anion of from 2 to about 22 carbon atoms containing 0 to 2 hydroxyl groups.

2. The organomodifed monosilyl compound of claim 1, wherein $R^1$ is a branched alkyl group $CR^6R^7R^8(CR^9R^{10})_m(CR^{11}R^{12})_n CHR^{13}CH_2$— in which $R^6$, $R^7$, $R^8$, $R^9$, $R^{10}$, $R^{11}$, $R^{12}$ and $R^{13}$ each independently is hydrogen or methyl, from 2 to 4 of $R^6$, $R^7$, $R^8$, $R^9$, $R^{10}$, $R^{11}$, $R^{12}$ and $R^{13}$ are methyl and subscripts m and n each independently is 0 or 1.

3. The organomodified monosilyl compound of claim 2, wherein $R^1$ contains from 2 to 4 methyl groups, $CR^6R^7R^8$ is $H_3C$—, $(H_3C)_2CH$— or $(H_3C)_3C$—, subscripts m and/or n are 0, Z is $R^2$ and $R^2$ is —$CH_2CH_2CH_2$—O—$(C_2H_4O)_a(C_3H_6O)_b$—$R^4$ in which $R^4$ is hydrogen, linear or branched alkyl of from 1 to 4 carbon atoms or an acyl group, subscript a is from 1 to about 20, subscript b is from 0 to about 10 and the sum of subscripts a and b is from 1 to about 20.

4. The organomodified monosilyl compound of claim 3, wherein subscript a is from 2 to about 15.

5. The organomodified monosilyl compound of claim 4, wherein subscript b is from 0 to about 6 and the sum of subscripts a and b is from 2 to about 15.

6. The organomodified monosilyl compound of claim 3, wherein subscript a is from 4 to about 10.

7. The organomodified monosilyl compound of claim 6, wherein subscript b is from 0 to about 4 and the sum of subscripts a and b is from about 4 to about 10.

8. The organomodified monosilyl compound of claim 3, wherein subscript b is from 0 to about 6.

9. An agrochemical composition comprising a wetting agent-effective amount of at least one organomodified monosilyl compound of claim 8.

10. An agrochemical composition comprising a wetting agent-effective amount of at least one organomodified monosilyl compound of claim 3.

11. The organomodified monosilyl compound of claim 2, wherein $R^1$ contains from 2 to 4 methyl groups, $CR^6R^7R^8$ is $H_3C$—, $(H_3C)_2CH$— or $(H_3C)_3C$—, m and/or n are 0 or 1, Z is $R^3$ and $R^3$ is —$CH_2CH_2CH_2$—O—$CH_2$(OH)—$CH_2$—$N^+(CH_3)_2$—$R^5$ [$X^-$] in which $R^5$ is a linear or branched alkyl of from 1 to about 4 carbon atoms.

12. An agrochemical composition comprising a wetting agent-effective amount of at least one organomodified monosilyl compound of claim 11.

13. The organomodified monosilyl compound of claim 2, wherein $R^1$ contains from 2 to 4 methyl groups, $CR^1R^2R^3$ is $(H_3C)_2CH$— or $(H_3C)_3C$—, m is 0 or 1, n is 0, Z is $R^3$ and $R^3$ is —$CH_2CH_2CH_2$—O—CH(OH)—$CH_2$—$N^+(CH_3)_2$—$R^5$ [$X^-$] in which $R^5$ is a linear or branched alkyl group of from 1 to about 4 carbon atoms and $X^-$ is a carboxylate anion of from 2 to about 10 carbon atoms and from 0 to 2 hydroxyl groups.

14. The organomodified compound of claim 13, wherein $X^-$ is a carboxylate anion of from 2 to about 6 carbon atoms and from 0 to 2 hydroxyl groups.

15. An agrochemical composition comprising a wetting agent-effective amount of at least one organomodified monosilyl compound of claim 13.

16. The organomodified monosilyl compound of claim 2 which is at least one ether- or polyether-modified monosilyl compound selected from the group consisting of:

| $CR^6R^7R^8(CR^9R^{10})_m(CR^{11}R^{12})_n$—$CHR^{13}$—$CH_2$—Si(CH$_3$)$_2$— | —Z |
|---|---|
| $(H_3C)_2CHCH_2CH_2$—Si(CH$_3$)$_2$— | —$CH_2CH_2CH_2$—O—$(C_2H_4O)_{7.5}$H |
| $(H_3C)_3CCH_2CH_2$—Si(CH$_3$)$_2$— | —$CH_2CH_2CH_2$—O—$(C_2H_4O)_{7.5}CH_3$ |
| $(H_3C)_2CHCH_2CH_2$—Si(CH$_3$)$_2$— | —$CH_2CH_2CH_2$—O($CH_2H_4O)_5(C_3H_6O)_{2.5}$H |
| $(CH_3)_2CHCH(CH_3)CH(CH_3)CH_2$—Si(CH$_3$)$_2$— | —$CH_2CH_2CH_2$—O—$(CH_2CH_2O)_4$H |
| $H_3CCH_2CH(CH_3)CH_2CH_2$—Si(CH$_3$)$_2$— | —$CH_2CH_2CH_2$—O—$(C_2H_4O)_{7.5}$H |
| $H_3CCH_2C(CH_3)_2CH_2CH_2$—Si(CH$_3$)$_2$— | —$CH_2CH_2CH_2$—O—$(C_2H_4O)_{7.5}$H |
| $(H_3C)_2CHCH(CH_3)CH_2$—Si(CH$_3$)$_2$— | —$CH_2CH_2CH_2$—O—$(C_2H_4O)_{7.5}CH_3$ |
| $H_3CCH_2C(CH_3)_2C(CH_3)CH_2$—Si(CH$_3$)$_2$— | —$CH_2CH_2CH_2$—O($CH_2H_4O)_5(C_3H_6O)_{2.5}$H |
| $(H_3C)_2CHCH_2CH_2$—Si(CH$_3$)$_2$— | —$CH_2CH_2CH_2$—O—$(CH_2CH_2O)_5$H |
| $(H_3C)_3CCH_2CH_2$—Si(CH$_3$)$_2$— | —$CH_2CH_2CH_2$—O—$CH_2CH_2OH$ |
| $(H_3C)_2CHCH(CH_3)CH_2$—Si(CH$_3$)$_2$— | —$CH_2CH_2CH_2$—O—$(C_2H_4O)_{7.5}$H |
| $(H_3C)_3CCH_2CH_2$—Si(CH$_3$)$_2$— | —$CH_2CH_2CH_2$—O($CH_2H_4O)_5(C_3H_6O)_{2.5}$H. |

17. An agrochemical composition comprising a wetting agent-effective amount of at least one organomodified monosilyl compound of claim 16.

18. The organomodified monosilyl compound of claim 2 which is at least one quaternary ammonium-modified monosilyl compound selected from the group consisting of:

| $CR^6R^7R^8(CR^9R^{10})_m(CR^{11}R^{12})_n$—$CHR^{13}$—$CH_2$—$Si(CH_3)_2$— | —Z |
|---|---|
| $(H_3C)_2CHCH_2CH_2CH_2$—$Si(CH_3)_2$— | —$CH_2CH_2CH_2$—O—$CH(OH)CH_2N^+(CH_3)_2$—$CH_2CH_3[CH_3CH_2COO^-]$ |
| $(H_3C)_2CHCH(CH_3)CH_2$—$Si(CH_3)_2$— | —$CH_2CH_2CH_2$—O—$CH(OH)CH_2N^+(CH_3)_2$—$CH_2CH_3[CH_3CH_2COO^-]$ |
| $H_3CCH_2C(CH_3)_2C(CH_3)CH_2$—$Si(CH_3)_2$— | —$CH_2CH_2CH_2$—O—$CH(OH)CH_2N^+(CH_3)_2$—$CH_2CH_3[(CH_2OH)_2(CH_3)C—COO^-]$ |
| $(H_3C)_3CCH_2CH_2$—$Si(CH_3)_2$— | —$CH_2CH_2CH_2$—O—$CH(OH)CH_2N^+(CH_3)_2$—$CH_2CH_3[CH_2(OH)_2(CH_3)C—COO^-]$ |
| $(H_3C)_3CCH_2CH_2$—$Si(CH_3)_2$— | —$CH_2CH_2CH_2$—O—$CH_2CH(OH)CH_2N^+(CH_3)_2$—$CH_2CH_2CH_2OH[(CH_2OH)_2(CH_3)C—COO^-]$ |
| $(H_3C)_2CHCH_2CH_2$—$Si(CH_3)_2$— | —$CH_2CH_2CH_2$—O—$CH(OH)CH_2N^+(CH_3)_2$—$CH_2CH_3 [CH_3CH_2COO^-]$ |
| $(H_3C)_2CHCH(CH_3)CH(CH_3)CH_2$—$Si(CH_3)_2$— | —$CH_2CH_2CH_2$—O—$CH(OH)CH_2N^+(CH_3)_2$—$CH_2CH_3 [CH_2(OH)CH_2COO^-]$ |
| $H_3CCH_2CH(CH_3)CH_2CH_2$—$Si(CH_3)_2$— | —$CH_2CH_2CH_2$—O—$CH(OH)CH_2N^+(CH_3)_2$—$CH_2CH_3 [CH_2(OH)CH_2COO^-]$ |
| $H_3CCH_2C(CH_3)_2CH_2CH_2$—$Si(CH_3)_2$— | —$CH_2CH_2CH_2$—O—$CH(OH)CH_2N^+(CH_3)_2$—$CH_2CH_3 [CH_2(OH)CH_2COO^-]$ |
| $(H_3C)_2CHCH_2CH_2$—$Si(CH_3)_2$— | —$CH_2CH_2CH_2$—O—$CH(OH)CH_2N^+(CH_3)_2$—$CH_2CH_3 [CH_2(OH)CH_2CH_2COO^-]$ |
| $H_3CC(CH_3)_2CH_2CH_2CH_2$—$CH_2$—$Si(CH_3)_2$— | —$CH_2CH_2CH_2$—O—$CH(OH)CH_2N^+(CH_3)_2$—$CH_2CH_3 [CH_2(OH)CH_2COO^-]$. |

19. An agrochemical composition comprising a wetting agent-effective amount of at least one organomodified monosilyl compound of claim 2.

20. An agrochemical composition, cosurfactant, coating, personal care product or home care product comprising a wetting agent-effective amount of at least one organomodified monosilyl compound of claim 1.

21. An agrochemical composition comprising a wetting agent-effective amount of at least one organomodified monosilyl compound of claim 18.

* * * * *